(12) United States Patent
Flick et al.

(10) Patent No.: US 6,689,079 B2
(45) Date of Patent: Feb. 10, 2004

(54) SUPPORT DEVICE WITH PRESSURE ADJUSTMENT SECTION AND METHOD OF USE

(75) Inventors: Roland E. Flick, Elma, NY (US); Michael P. Rechin, Silver Creek, NY (US)

(73) Assignee: Gaymar Industries, Inc., Orchard Park, NY (US)

( * ) Notice: Subject to any disclaimer, the term of this patent is extended or adjusted under 35 U.S.C. 154(b) by 0 days.

(21) Appl. No.: 10/195,691

(22) Filed: Jul. 12, 2002

(65) Prior Publication Data

US 2003/0028135 A1 Feb. 6, 2003

Related U.S. Application Data (60) Provisional application No. 60/305,234, filed on Jul. 13, 2001.

(51) Int. Cl.[7] .................................................. A61F 5/00
(52) U.S. Cl. ............................ 602/13; 602/14; 602/27; 128/882; 128/DIG. 20
(58) Field of Search ................................ 602/5, 13, 14, 602/23, 27, 60–65; 128/882, DIG. 20, 846, 869, 892, 894

(56) References Cited

U.S. PATENT DOCUMENTS

| | | |
|---|---|---|
| 2,028,060 A | 1/1936 | Gilbert |
| 3,186,405 A | 6/1965 | Bailey et al. |
| 4,361,969 A | 12/1982 | Vermonet |
| 4,454,615 A | 6/1984 | Whitney |
| 4,483,030 A | 11/1984 | Flick et al. |
| 4,724,627 A | 2/1988 | Sisco |
| 4,860,397 A | 8/1989 | Gusakov |
| 4,912,861 A | 4/1990 | Huang |
| 4,945,588 A | 8/1990 | Cassidy et al. |
| 4,969,459 A | 11/1990 | Gusakov |
| 5,068,935 A | 12/1991 | Hagopian |
| 5,072,468 A | 12/1991 | Hagopian |
| 5,109,165 A | 4/1992 | Gusakov |
| 5,140,309 A | 8/1992 | Gusakov |
| 5,144,708 A | 9/1992 | Pekar |
| 5,179,792 A | 1/1993 | Brantingham |
| 5,183,039 A | 2/1993 | Sarian et al. |
| 5,184,112 A | 2/1993 | Gusakov |
| 5,237,501 A | 8/1993 | Gusakov |
| D343,531 S | 1/1994 | Hagopian |
| 5,328,445 A | 7/1994 | Spahn et al. |
| 5,329,640 A | 7/1994 | Hourigan |
| 5,329,705 A | 7/1994 | Grim et al. |
| D351,071 S | 10/1994 | Hagopian |
| 5,353,525 A | 10/1994 | Grim |
| RE34,883 E | 3/1995 | Grim |
| 5,400,529 A | 3/1995 | Bell et al. |
| 5,406,661 A | 4/1995 | Pekar |
| 5,416,988 A | 5/1995 | Potter et al. |
| 5,435,009 A | 7/1995 | Schild et al. |
| 5,489,259 A | 2/1996 | Jacobs et al. |
| D368,525 S | 4/1996 | Karten et al. |
| 5,588,956 A | 12/1996 | Billotti |
| 5,613,941 A | 3/1997 | Prengler |
| 5,638,565 A | 6/1997 | Pekar |
| 5,745,939 A | 5/1998 | Flick et al. |
| 5,761,834 A | 6/1998 | Grim et al. |

(List continued on next page.)

FOREIGN PATENT DOCUMENTS

| | | |
|---|---|---|
| EP | 0 558 713 | 3/1998 |
| GB | 2 346 809 | 4/2002 |
| JP | 6503438 | 8/1992 |

*Primary Examiner*—Danton D. DeMille
*Assistant Examiner*—Quang D Thanh
(74) *Attorney, Agent, or Firm*—Kevin D. McCarthy; Roach, Brown, McCarthy & Gruber, PC (57) ABSTRACT

A protective and pressure normalizing device including a support member having an exterior wall and an interior wall which define a first chamber, wherein the support member comprises a pressure adjustment section movable between a first position and at least one second position to adjust a pressure of a medium within the first chamber.

39 Claims, 9 Drawing Sheets

U.S. PATENT DOCUMENTS

| | | |
|---|---|---|
| 5,765,564 A | 6/1998 | Ewing |
| 5,787,531 A | 8/1998 | Pepe |
| 5,794,289 A | 8/1998 | Wortman et al. |
| 5,813,144 A | 9/1998 | Prengler |
| 5,875,282 A | 2/1999 | Jordan et al. |
| 5,893,219 A | 4/1999 | Smith et al. |
| 5,901,393 A | 5/1999 | Pepe et al. |
| 5,926,883 A | 7/1999 | Rechin et al. |
| 5,957,872 A | 9/1999 | Flick |
| 6,061,855 A | 5/2000 | Flick |
| 6,079,070 A | 6/2000 | Flick |
| 6,099,951 A | 8/2000 | Flick et al. |
| 6,131,469 A | 10/2000 | Wortman et al. |
| 6,138,382 A | 10/2000 | Schoesler |
| 6,145,142 A | 11/2000 | Rechin et al. |
| 6,152,169 A | 11/2000 | Flick |
| 6,189,172 B1 | 2/2001 | Baek |
| 6,200,284 B1 | 3/2001 | Flick |
| 6,357,491 B1 | 3/2002 | Buchanan et al. |
| 6,375,633 B1 | 4/2002 | Endress et al. |
| 6,447,865 B1 | 9/2002 | Flick et al. |
| 6,488,043 B2 | 12/2002 | Flick |
| 6,517,510 B1 | 2/2003 | Stewart et al. |
| 2002/0151243 A1 | 10/2002 | Flick et al. |
| 2002/0187332 A1 | 12/2002 | Flick et al. |
| 2003/0028157 A1 | 2/2003 | Jusiak et al. |

SUPPORT DEVICE WITH PRESSURE ADJUSTMENT SECTION AND METHOD OF USE

The present invention claims the benefit of U.S. Provisional Patent Application Ser. No. 60/305,234, filed Jul. 13, 2001, which is hereby incorporated by reference in its entirety.

FIELD OF THE INVENTION

The present invention generally relates to devices and methods for stabilizing and supporting a structure, especially a body part of a user. The invention, more specifically, is an inflatable device that provides protection for, and relieves pressure on the body part, especially when the body is in a supine or semi-Fowler's position

BACKGROUND OF THE INVENTION

Devices for supporting a body extremity have been developed. For example, U.S. Pat. No. 5,489,259 to Jacobs et al. ("Jacobs") relates to a pressure-normalizing single-chambered static pressure device for supporting and protecting a body extremity, in particular a heel. That device has an inflatable member with exterior and interior surfaces, a plurality of seams to connect the exterior and interior surfaces together along a line corresponding to the Achilles' tendon and the ankle bones, a plurality of apertures along those seams, and a nozzle.

In order to inflate the Jacobs' device, an external pump is attached to the nozzle and the device is inflated to a predetermined pressure by a third party or the patient, then the device is left alone and is said to conform to the extremity.

A problem with devices, such as those described in Jacobs, is that the device may be over-inflated or even under-inflated. Such results may become deleterious to the patient. In addition, when the devices are inflated with air, there is a significant risk of cross-contamination caused by different individuals orally adjusting the pressure of the medium through the nozzle. Moreover, an external device, such as a pump, is required to adjust the pressure of the medium within the device even after the device is initially inflated to a desired level, to make modifications for climatic conditions, changes in elevation, or leakage.

SUMMARY OF THE INVENTION

The present invention relates to a protective and pressure normalizing device. The device includes a support member having an exterior wall and an interior wall which define a first chamber. The support member includes a pressure adjustment section movable between a first position and at least one second position to adjust a pressure of a medium within the first chamber.

The present invention also relates to a protective and pressure normalizing device for a body extremity. The device includes a support member having an exterior wall and an interior wall which define a first chamber and a joint aperture. The support member comprises a pressure adjustment section movable between a first position and at least one second position to adjust a pressure of a medium within the first chamber and the support member and pressure adjustment section are in communication for the transfer of the medium therebetween.

Another aspect of the present invention relates to a method for protecting and normalizing the pressure on a structure. The method involves providing a support member including an exterior wall and an interior wall which define a first chamber and a pressure adjustment section movable between a first position and at least one second position to adjust a pressure of a medium within the first chamber. A structure in positioned in the support member.

In the device and method of the present invention, the pressure of the medium within the device is adjusted through repositioning of a pressure adjustment section. By adjusting the pressure of the medium through repositioning of the pressure adjustment section, the need for external devices, such as pumps, to adjust the pressure of the medium is eliminated. In addition, when the medium is air, the risk of cross-contamination caused by orally adjusting the pressure of the medium is eliminated in the present invention. Thus, the device can be shipped sealed and pre-inflated to a low pressure and the pressure easily adjusted on-site by the user.

The device of the present invention is adaptable to fit different sized body parts and can be worn on either a left or right extremity of the user. In addition, the device of the present invention minimizes pressure contact between the body part and any surface on which it is placed, for example, a hospital bed, thereby, decreasing the risk of the formation of decubitus ulcers on the body part as a result of such contact. Moreover, the device of the present invention limits contact between the body part of a user, especially the toe area of the foot, and objects in the user's surroundings such as sheets, blankets, etc.

In a specific embodiment, the device of the present invention is an inflatable device that provides protection for, and relieves pressure on the heel area of the foot, when the body is in a supine or semi-Fowler's position. When used to stabilize a foot, the device and method of the present invention can be used in order to prevent shortening of the Achilles tendon, i.e., "foot drop." Further, when used for the foot, the device separates the ankles, preventing them from crossing and thereby reducing additional pressure when the hips are rotated. In addition, the device allows for air circulation and provides protection for the sides and bottom of the foot or any other body part positioned in the device.

DETAILED DESCRIPTION OF THE INVENTION

The present invention relates to a device 10 including a support member 12 which includes a pressure adjustment section 14, where support member 12 and pressure adjustment section 14 form a single chamber. The pressure adjustment section 14 can be attached at any position on the support member 12 and can be provided, for example, as a tag or cuff. The support member 12 can be used to stabilize a body part (e.g., a body extremity) or any other structure. In addition, the device of the present invention minimizes pressure contact between the body part and any surface on which it is placed as well as other objects in the user's surrounding, thereby decreasing the risk of the formation of decubitus ulcers on the body part as a result of such contact.

FIGS. 1–4 show perspective views of a device 10 according to the present invention. Device 10 includes a support member 12 which has an exterior wall 16 and an interior wall 18 which define a chamber 20, shown in FIGS. 6–10. The support member 12 also includes a plurality of non-support regions 22, one or more securing devices 24, and an aperture for a joint of a user 26. In addition, the support member 12 includes a pressure adjustment section 14.

Figure 1:
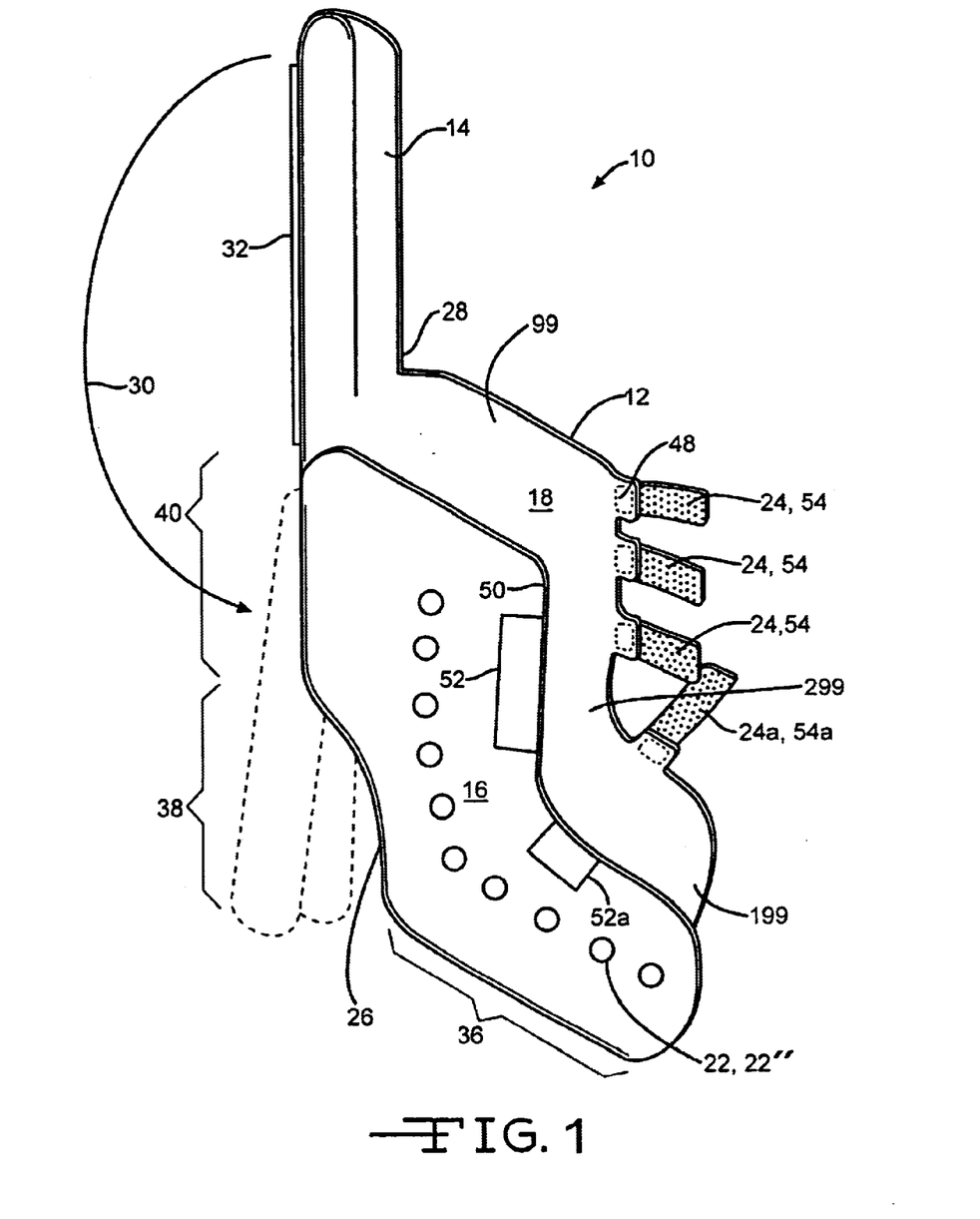
FIG. 1 is a perspective view of a first embodiment of the device of the present invention with a pressure adjustment section attached to a first end of the device.
Figure 2:
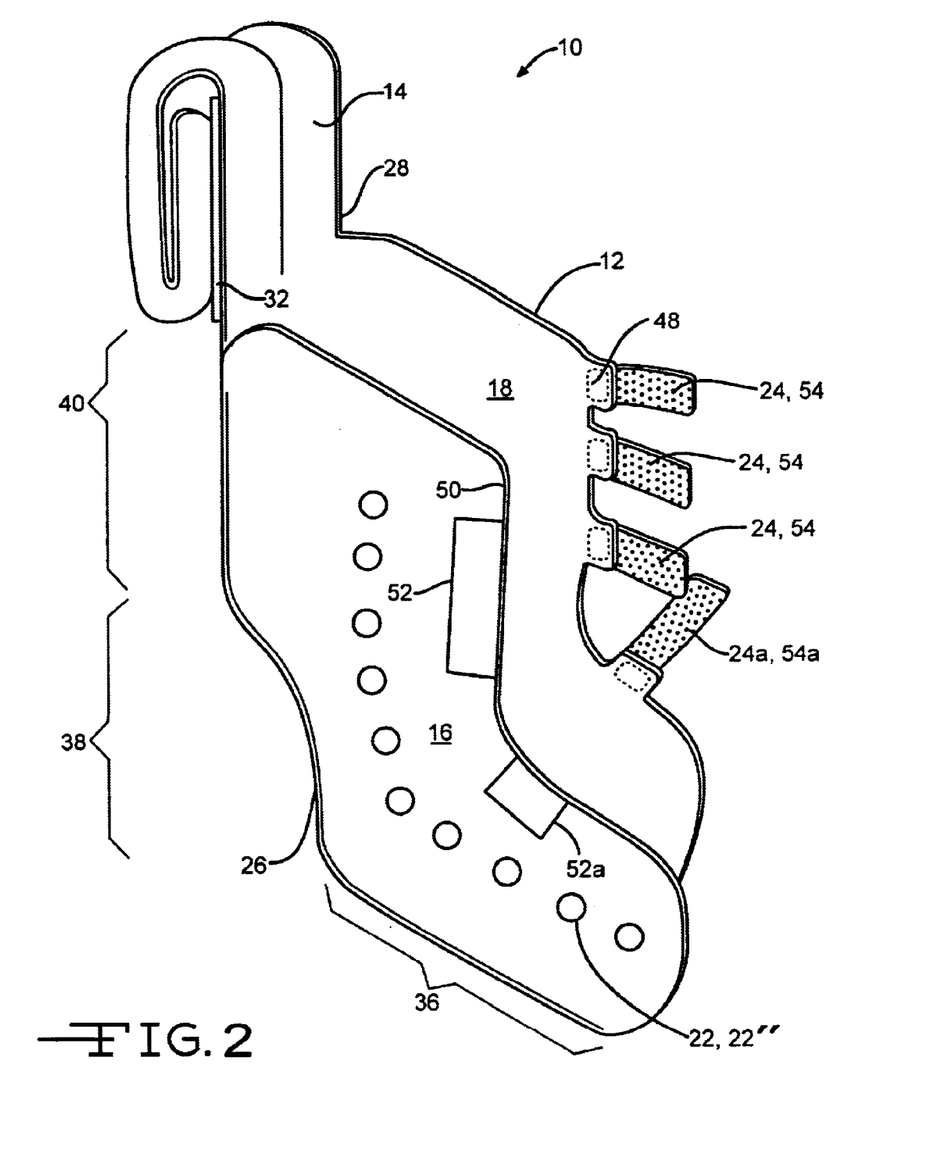
FIG. 2 is a perspective view of the device of FIG. 1 wherein the pressure adjustment section is repositioned into a second position.
Figure 3:
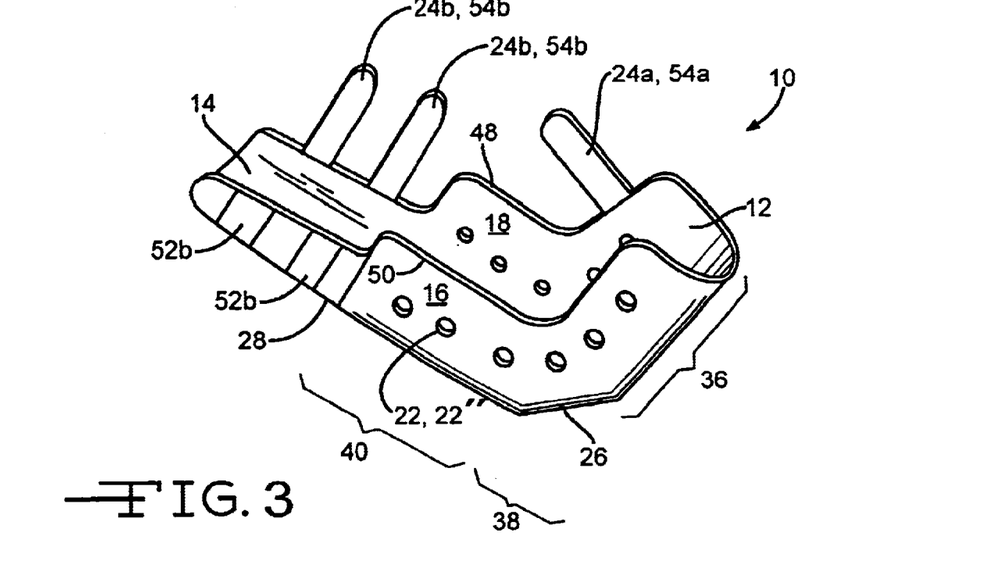
FIG. 3 is a perspective view of an alternative embodiment of the device of FIG. 1.
Figure 4:
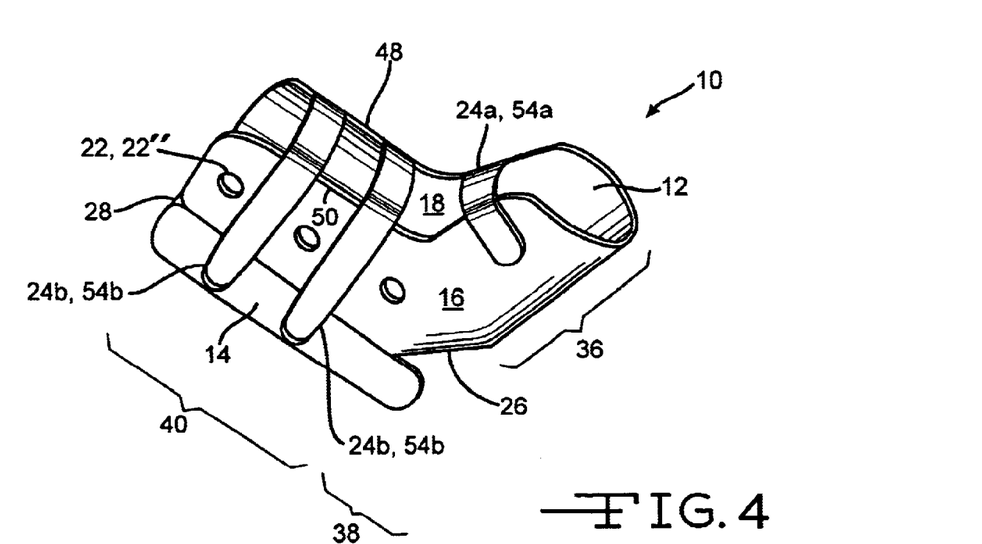
FIG. 4 is a perspective view of the device of FIG. 3 wherein the pressure adjustment section is repositioned into a second position.

Referring to FIGS. 1–5, in this embodiment, the pressure adjustment section 14 extends from a first end 28 adjacent to the top edge of the support member 12 and is movable toward the joint aperture 26 of the support member 12 (i.e., from a first position to at least one second position). Also, as shown in FIGS. 1 and 3–4, the pressure adjustment section 14 is movable so that it extends adjacent (i.e., beneath) the joint aperture 26 of the support member 12. When the pressure adjustment section 14 is positioned so that it extends beneath the joint aperture 26, it provides additional support for the joint, such as the heel. As shown in FIG. 2, the pressure adjustment section 14 is movable so that it folds upon itself. However, the pressure adjustment section 14 may be any suitable size or shape, for example, a tag or cuff, such that the pressure of the medium within the chamber 20 can be adjusted when the device is placed on a user by repositioning the pressure adjustment section 14 to any desired position. In particular, when the pressure adjustment section is repositioned to a second position, the volume available for the medium to occupy in the device 10 is decreased, thereby adjusting the pressure of the medium within the chamber 20.

In this particular embodiment, the pressure adjustment section 14 includes an attachment device 32 for attaching at least a first portion of the pressure adjustment section 14 to at least a portion of the support member 12, or at least a second portion of the pressure adjustment section. In this particular embodiment, the attachment device is hoop and loop type fasteners. However, other suitable attachment devices include, but are not limited to, adhesives, buttons, and buckles. The attachment device 32 secures the pressure adjustment section 14 when repositioned.

Figure 12:
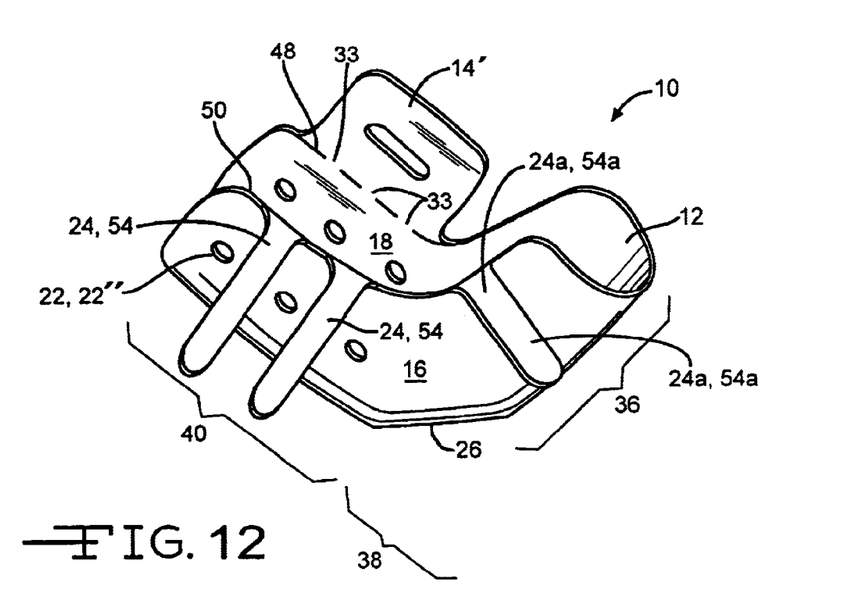
FIG. 12 is a perspective view of a second embodiment of the device of the present invention.
Figure 13:
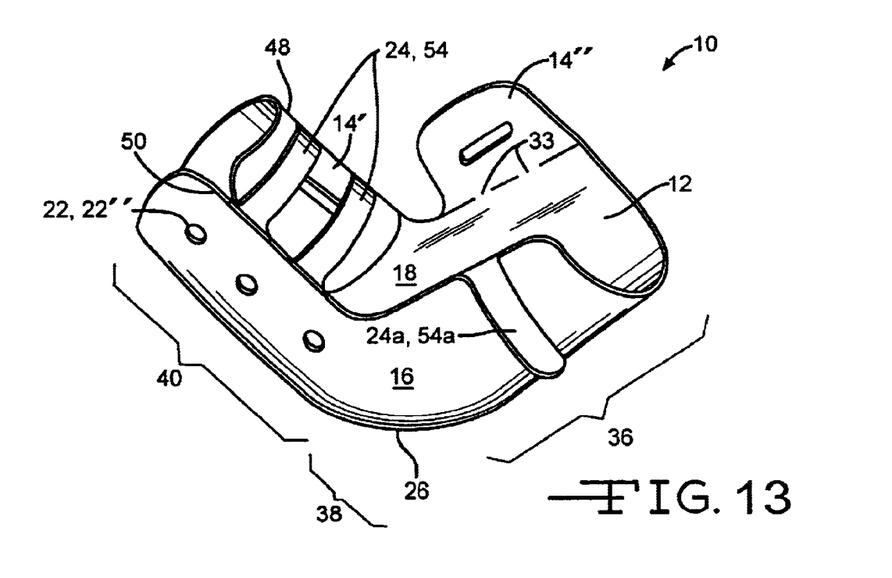
FIG. 13 is a perspective view of a third embodiment of the device of the present invention.

As shown in FIGS. 1–6, the pressure adjustment section 14 forms a part of a single chamber 20 with the support member 12. However, the pressure adjustment section 14 may be a separate chamber which is interconnected with chamber 20 through at least one medium transfer channel 33, as shown in FIGS. 12–13.

The support member 12 with non-support regions 22 and pressure adjustment section 14 has an exterior wall 16 and an interior wall 18. The exterior and interior walls 16, 18 can be constructed of the same or different materials.

The interior wall 18 is constructed of a lightweight cotton, gauze, paper, or synthetic material which may be woven or non-woven, or any other material that is breathable and suitable for use in a hospital, alternative care, or home care environment, when the device is used to support a body part. The interior wall 18 is strong enough to secure a body part of a user and capable of being comfortably placed in contact with the body part of a user. In use, at least a portion of the interior wall 18 of the support member 12 contacts at least a portion the body part of the user.

The exterior wall 16 can be constructed of any type of material so long as it meets some minimal characteristics. These minimal characteristics, which apply to both materials 16 and 18, when the device is used to support a body part, include not applying excessive shear force to a user's tissue, providing adequate wicking characteristics so that moisture is drawn away from the skin of the body part to keep the body part at a normal temperature, and providing sufficient flexibility and pliability to conform readily to the shape of the user's body part. The exterior wall 16 and interior wall 18 may be constructed to be disposable or reusable.

In an alternative embodiment, the exterior wall 16 may include an exterior reinforcing material layer and the interior wall 18 may include an interior wicking material layer to cool and wick moisture. The exterior reinforcing material layer and interior wicking material layer may be made of the same or different materials than the exterior wall 16 and interior wall 18. In this embodiment, at least a portion of the interior wicking material layer contacts at least a portion of the body part of the user.

Referring to FIGS. 1–4, the device 10 is divided into at least three distinct components 36, 38, and 40, that correspond to a body extremity having a joint (elbow, knee, or heel/ankle) of a user. However, the device 10 may be divided into any number of components. The body extremity is divided into a posterior, anterior, and the two other sides.

As shown in FIGS. 1–4, the components are a lower portion 36, an intermediate portion 38, and an upper portion 40. The interior wall 18 of the lower portion 36 contacts at least parts of the anterior and other sides of the foot (i.e., a lower region of the body extremity). The interior wall 18 of the intermediate portion 38 contacts at least a portion of the other sides of the body extremity that corresponds to the heel, which is on the posterior side of the body extremity (i.e., an intermediate region of the body extremity) and includes the joint aperture 26. The interior wall 18 of the upper portion 40 contacts at least a portion of the posterior and other sides of the calf of the body extremity (i.e., an upper portion of the body extremity). Although the device 10 shown in FIGS. 1–4 relates to the ankle, heel, and foot of a user, the device may be used with other body parts, e.g., a knee or an elbow, and the interior wall 18 would contact surfaces of the body part other than that described above.

The joint aperture 26 exposes the joint of the body part. In this example, the joint is the heel; however, the joint could be any suitable joint, such as the elbow or knee. Although this particular embodiment includes a joint aperture 26, the device could be provided without a joint aperture. Since we are on the topic of apertures, we will generically describe the other apertures of the present invention that are illustrated in FIG. 1. These other apertures include a proximal aperture 99, a distal aperture 199, and a gap aperture 299.

Collectively, the proximal aperture 99 and the distal aperture 199 are referred to as end apertures. In this embodiment that has a heel aperture, the proximal aperture 99 would allow a calf of a leg to extend therefrom, the distal aperture 199 would allow toes to extend therefrom, and the gap aperture 299 would receive the portions of the leg and foot that do not extend beyond the proximal and distal apertures 99, 199.

Figure 5:
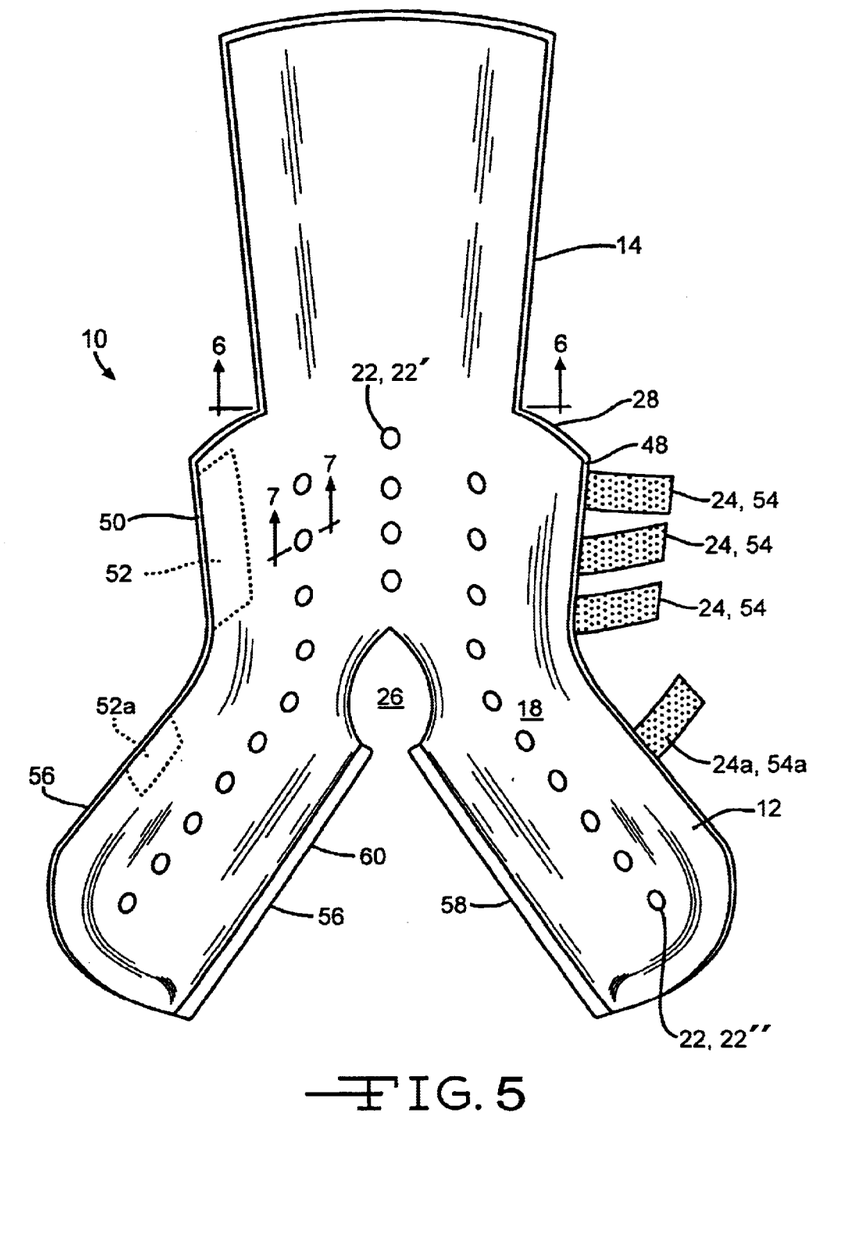
FIG. 5 is a perspective view of the device of FIG. 1 showing edges 58 and 60 which are joined to form the device of FIG. 1.
Figure 6:
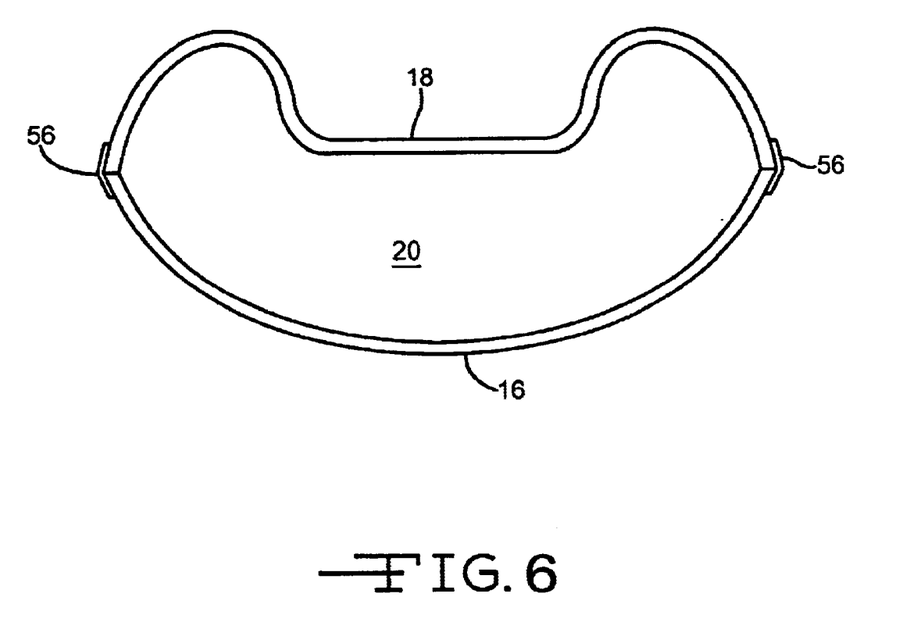
FIG. 6 is a cross-sectional view of FIG. 5 taken along the lines 6—6.

To relieve pressure on the body part, the support member 12 has a plurality of non-support regions 22 interspaced throughout it. In one embodiment, shown in FIG. 5, there is a first set of non-support regions 22' positioned along a line corresponding to an Achilles' tendon of the calf. A second set of the non-support regions 22" are positioned along a line corresponding to the ankle bone of the body extremity. Each of the non-support regions 22', 22" is interspaced from the others, as shown in FIG. 5, and highlighted in FIG. 7—a cross-section of FIG. 5 taken along the lines 7—7.

Figure 7:
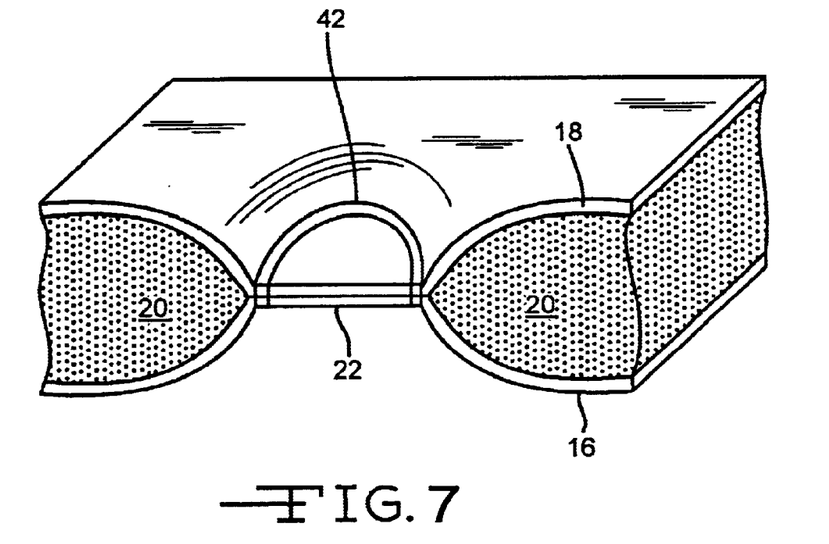
FIG. 7 is a cross-sectional view of FIG. 5 taken along the lines 7—7.
Figure 8:
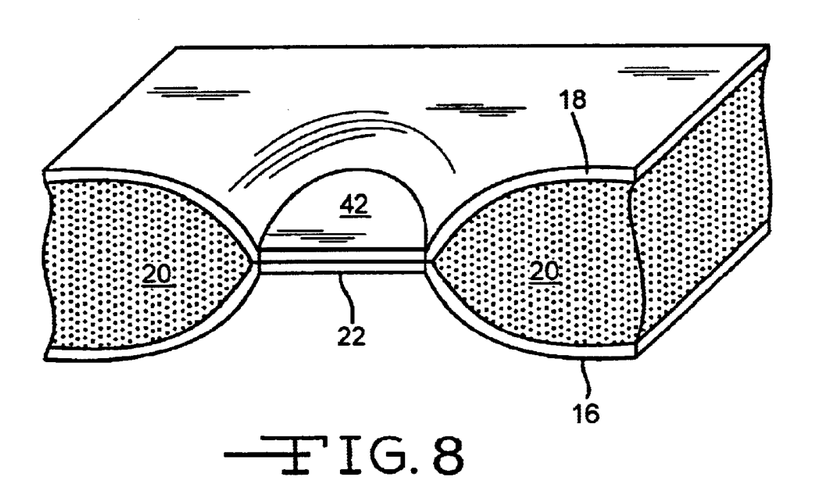
FIG. 8 is an another embodiment of FIG. 7.
Figure 9:
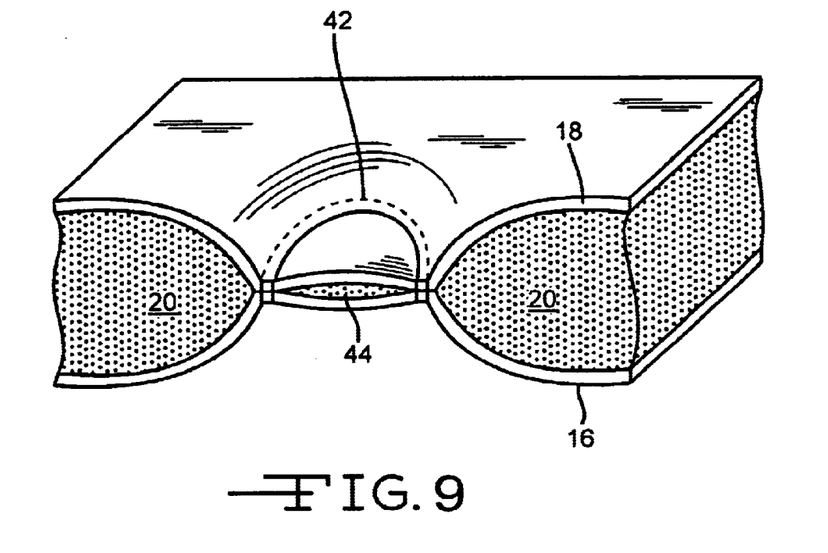
FIG. 9 is an another embodiment of FIG. 7.
Figure 10:
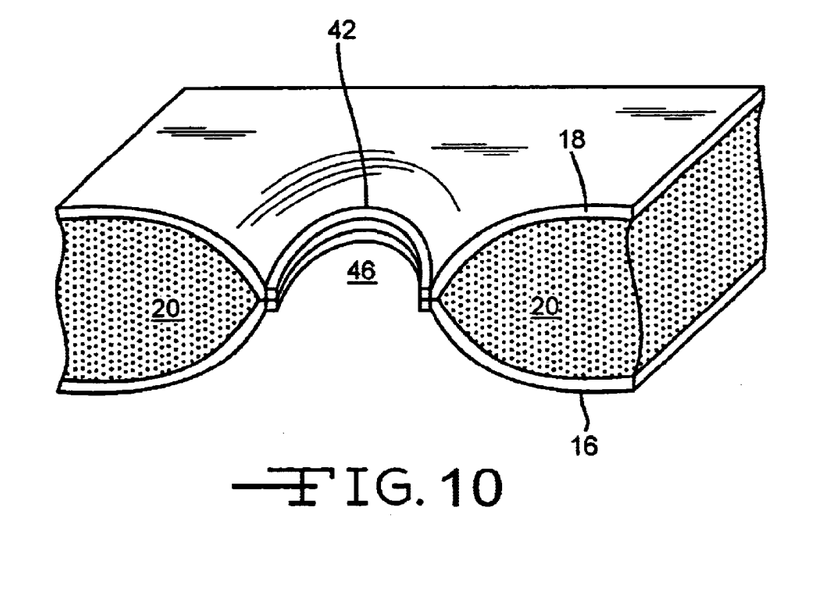
FIG. 10 is an another embodiment of FIG. 7.

As shown in FIG. 7, the non-support region 22 is formed by bonding predetermined portions of the interior wall 18 to the exterior wall 16 at predetermined point 42. In some embodiments, the predetermined point 42 is a pre-selected area of the non-support region 22 wherein the remainder of the non-support region 22 is flat, as shown in FIG. 7, or the predetermined point 42 is the entire non-support region 22 as shown in FIG. 8 (an alternative embodiment of FIG. 7), or the predetermined point 42 is a pre-selected area of the non-support region 22 wherein the remainder of the region 22 is filled with a fluid or a predetermined piece of material 44, as shown in FIG. 9 (an alternative embodiment of FIG. 7), or the predetermined point 42 is a pre-selected area of the non-support region 22 wherein within a predetermined portion of the remainder of the region 22 is an aperture 46, as shown in FIG. 10 (an alternative embodiment of FIG. 7). The predetermined point 42 can be made by a heat-seal, ultrasonic sound, or other conventional means.

Referring to FIGS. 6–10, the exterior wall 16 and interior wall 18 of the support member 12 form a chamber 20 which includes a medium having an initial predetermined pressure. For example, the chamber 20 of the support member 12 including the pressure adjustment section 14 is filled with a medium to a pressure of about 0–50 mmHg. In one embodiment, the chamber 20 of the support member is filled with a medium to a pressure of about 0–15 mmHg. Such pressures minimize stretch of the interior and exterior walls 16, 18 of the support member 12 due, for example, to elevation or temperature changes. However, any desired pressure can be used. In addition, any suitable medium can be used. The medium is typically a fluid, such as gases (e.g., air) or liquids (e.g., water), suspensions, gelastic materials, as sold by EdiZone, Inc. of Utah, or any other material that reduces pressure on the body part.

In this embodiment, the chamber 20 is pre-filled with medium at a pre-determined pressure with no means to inflate or deflate the device 10 without destroying it. The pressure of the medium is then adjusted by repositioning the pressure adjustment section 14. By adjusting the pressure of the medium through repositioning of the pressure adjustment section 14, the need for external devices, such as pumps, to adjust the pressure of the medium is eliminated. In addition, when the medium is air, the risk of cross-contamination caused by orally adjusting the pressure of the medium is eliminated in the present invention. Thus, the device can be shipped sealed and pre-inflated to a low pressure and the pressure easily adjusted on-site by the user.

Figure 11:
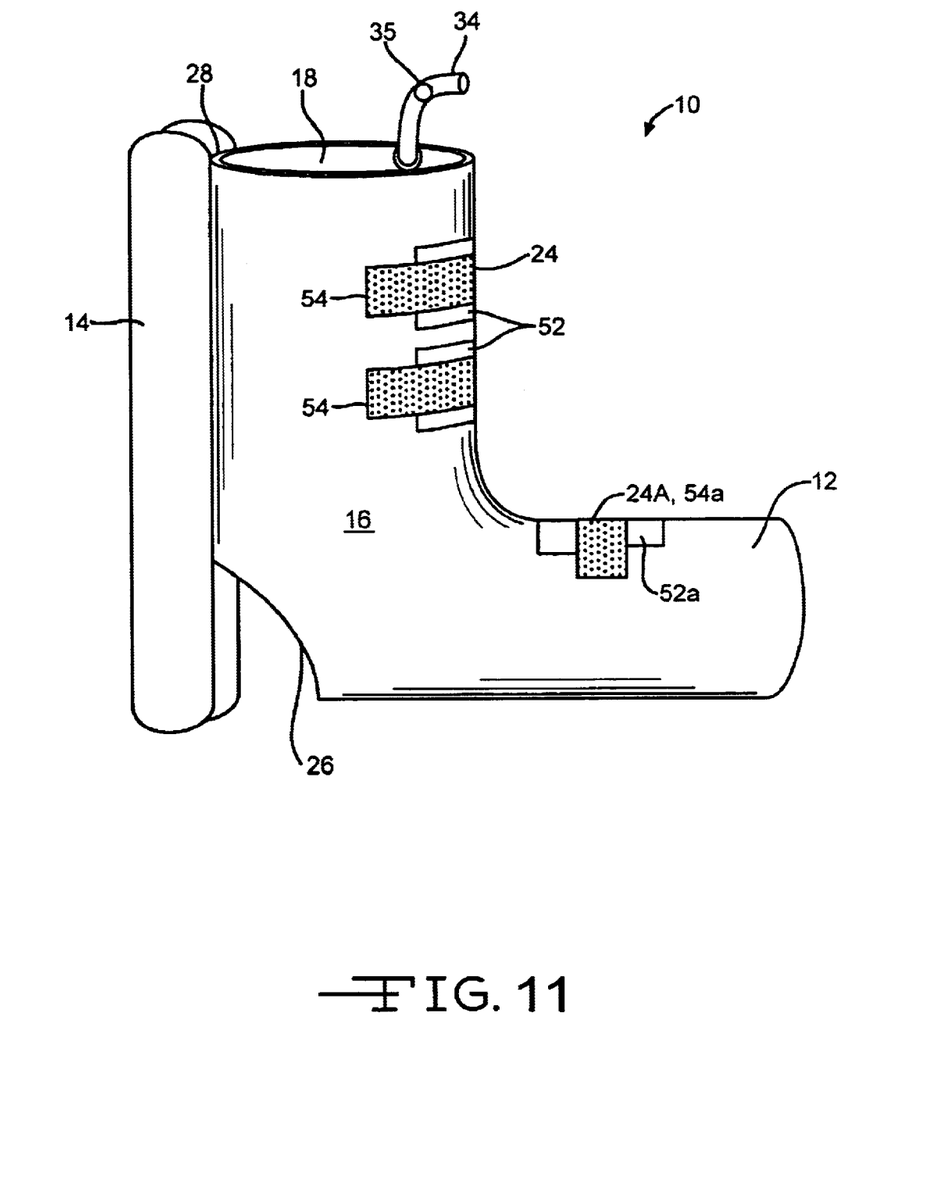
FIG. 11 is a side perspective view of an alternative embodiment of the device of FIG. 1 including a nozzle.

FIG. 11 illustrates an alternative embodiment of the device of FIG. 1 without any non-support regions 22 and with a nozzle 34. In this embodiment, the device may be filled or adjusted by the user through nozzle 34 to an initial predetermined pressure. The nozzle 34 may have a conventional check valve 35 within the nozzle. The pressure of the medium is then adjusted by repositioning the pressure adjustment section 14, as described above.

Referring to FIGS. 1–5 and 11, the present invention includes a plurality of securing devices 24. Each securing device 24 may be a support surface or a non-support surface. In either embodiment, each securing device 24 secures first and second edges 48, 50 of support member 12 to within a desired distance of each other and prevents device 10 from disengaging with the body part. Each securing device 24 is divided into two units, a receiver 52 and an extender 54. In the embodiment shown in FIGS. 1, 2, 5, and 11, the extender 54 protrudes from edge 48. Receiver 52 receives the extender 54 and secures the extender 54 into a desired position. In the present embodiments, the receiver 52 is a loop device, and the extender 54 has a hook device that connects with the loop device, although any type of securing device may be used. The receiver 52 can be a single unit, as illustrated in FIGS. 1, 2, and 5, or separate units for each extender 54, as illustrated in FIGS. 3 and 11. In addition, the device may include one or a plurality of securing devices 24. To attain maximum engagement between the edges 48 and 50, each securing device 24 in each embodiment has a particular position such that receiver 52 receives securing device 24 at a 90° angle.

Referring back to FIGS. 1–5 and 11, an alternative securing device 24a is positioned on the lower portion 36 of the device 10. This alternative securing device 24a further secures the device to the body part and includes a receiver 52a and an extender 54a. However, the device 10 can be provided without the securing device 24a.

In yet another embodiment, one or more securing devices 24b can be positioned, if desired, on the pressure adjustment section 14, as shown in FIGS. 3–4. The one or more securing devices 24b secure the device 10 to the body part and include a receiver 52b and an extender 54b.

The device 10 illustrated in FIG. 5 is in a pre-assembled position. The device 10 is put together by joining the exterior wall 16 to the interior wall 18 at an edge 56. Once the edge 56 is sealed, normally by heat sealing, the two particular edges, 58 and 60, are further joined together to form the device 10.

A second embodiment of the device 10 is shown in FIG. 12. The device 10 shown in FIG. 12 is identical to the previous embodiments, except as described below. In this embodiment, the support member 12 includes pressure adjustment section 14'. In this particular embodiment, the pressure adjustment section 14' extends from first edge 48 along the upper portion 40 of the support member 12 and is foldable around the upper region of the body part, such as the lower leg, of the user.

A third embodiment of the device 10 is shown in FIG. 13. The device 10 shown in FIG. 13 is identical to the previous embodiments, except as described below.

In the embodiment shown in FIG. 13, the support member 12 includes pressure adjustment section 14' and pressure adjustment section 14". In this particular embodiment, the pressure adjustment section 14" extends from first edge 48 along the lower portion 36 of the support member 12 and is foldable around the lower region of the body part, such as the foot, of the user. However, the support member 12 may include any one or all pressure adjustment sections 14, 14' and 14". As shown in FIGS. 12–13, these embodiments of the present invention include a plurality of securing devices 24 which include an extender 54 which protrudes from edge 50.

In accordance with one embodiment of the present invention, the device 10 is pre-filled with a medium. By pre-filling the device 10, the user is less likely to cause damage to its body part. Many individuals ignore the fact that when the temperature and/or air pressure of the environment is altered the pressure within the device 10 is also altered. Therefore, by pre-filling the device 10, the user is unable to over inflate or under inflate the device 10.

The device 10 of the present invention can be used to stabilize a body part (e.g., a body extremity) or any other structure. For example, the device 10 can be used for stabilizing an ankle while relieving pressure on the heel of the foot, a knee while relieving pressure on the knee of the leg, or an elbow while relieving pressure on the elbow of the arm. The knee, ankle/heel, and elbow are collectively referred to as a flexible joint or a bendable joint. When used to stabilize a foot, the device and method of the present invention can be used in order to prevent shortening of the Achilles tendon, i.e., "foot drop."

In use, the user positions a body part, such as a leg, foot, or arm, in the support member 12. If present, the securing devices 24, 24a, and 24b are used to secure the support member 12 to the body part. The support member 12 is provided pre-filled with medium or the user fills/adjusts the chamber 20 of the support member to a predetermined initial pressure. The pressure adjustment section 14 is then folded toward at least a portion of the support member 12 or on itself to provide pressure adjustment. In particular, when the pressure adjustment section 14 is folded, the medium within the chamber is displaced, thereby adjusting the pressure of the medium. If desired, the pressure adjustment section may be folded over so that it extends beneath the joint aperture of the device 10, thereby providing additional support for the joint.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, the recited order of processing elements or sequences, or the use of numbers, letters, or other designations therefor, is not intended to limit the claimed process to any order except as may be specified in the claims.

What is claimed is:

1. A protective and pressure normalizing device comprising a support member having a support section and a pressure adjustment section, the support section and the pressure adjustment section have an exterior wall and an interior wall;

the support section has at least a joint aperture, at least two end apertures, and a gap aperture that extends between the two end apertures;

the gap aperture and the end apertures are capable of receiving at least a portion of an object, and the joint aperture is designed to receive the joint of the at least a portion of the object;

a first chamber is defined by the exterior wall and the interior wall, and is capable of receiving a medium;

the pressure adjustment section extends away from and above at least one end aperture and support section and in a first position of the protective and pressure normalizing device (a) the entire interior wall of the pressure adjustment section is unfolded and (b) the medium is contained within the first chamber, and the medium within the support section applies a first pressure to the exterior and interior walls;

the first pressure can be adjusted by folding and attaching at least a portion of the exterior wall of the pressure adjustment section to the exterior wall of the pressure adjustment section or the exterior wall of the support section.

2. The device according to claim 1 wherein the pressure adjustment section extends from a distal aperture or a proximal aperture of the support section and is movable toward the joint aperture of the support section.

3. The device according to claim 2 wherein the pressure adjustment section is movable to extend adjacent the joint aperture of the support section.

4. The device according to claim 1 wherein the pressure adjustment section further comprises an attachment device for attaching at least a first portion of the pressure adjustment section to at least a portion of the support section or at least a second portion of the pressure adjustment section.

5. The device according to claim 1 further comprising a wicking material layer adjacent the interior wall.

6. The device according to claim 1 further comprising a reinforcing material layer adjacent the exterior wall.

7. The device according to claim 1 wherein the first chamber is filled with the medium to a predetermined internal pressure.

8. The device according to claim 1 wherein the medium is air.

9. The device according to claim 1 wherein the support section and pressure adjustment section comprise a single chamber.

10. The device according to claim 1 wherein the pressure adjustment section is interconnected with the support section through at least one medium transfer channel.

11. The device according to claim 1 further comprising a plurality of interspaced non-support regions in the support section.

12. The device according to claim 1 wherein the support section comprises:

a lower portion, wherein at least a portion of the interior wall of the lower portion contacts at least a portion of a lower region of a body part;

an intermediate portion, wherein at least a portion of the interior wall of the intermediate portion contacts at least a portion of an intermediate region of the body part; and an upper portion, wherein at least a portion of the interior wall of the upper portion contacts at least a portion of an upper region of the body part.

13. The device of claim 1 further comprising one or more securing devices, wherein the one or more securing devices attach at least a portion of a first edge of the support section to at least a portion of a second edge of the support section.

14. A method for protecting and normalizing the pressure on a structure comprising:

providing a support member comprising a support section and a pressure adjustment section, the support section and the pressure adjustment section have an exterior wall and an interior wall; the support section has at least a joint aperture, at least two end apertures, and a gap aperture that extends between the two end apertures, the gap aperture and the end apertures are capable of receiving at least a portion of the structure, and the joint aperture is designed to receive the joint of the at least a portion of the structure; a first chamber is defined by the exterior wall and the interior wall, and is capable of receiving a medium; the pressure adjustment section extends away from and above at least one end aperture and support section and in a first position of the protective and pressure normalizing device (a) the entire interior wall of the pressure adjustment section is unfolded and (b) the medium is contained within the first chamber, and the medium within the support section applies a first pressure to the exterior and interior walls; the first pressure can be adjusted by folding and attaching at least a portion of the exterior wall of the pressure adjustment section to the exterior wall of the pressure adjustment section or the exterior wall of the support section; and positioning the structure in the support member.

15. The method according to claim 14 further comprising: filling the first chamber with the medium to an initial predetermined pressure.

16. The method according to claim 14 wherein the pressure adjustment section extends from a distal aperture or a proximal aperture of the support section and is movable toward the joint aperture of the support section.

17. The method according to claim 16 wherein the pressure adjustment section is movable to extend adjacent the joint aperture of the support section.

18. The method according to claim 14 further comprising attaching at least a first portion of the pressure adjustment section to at least a portion of the support section or at least a second portion of the pressure adjustment section using an attachment device.

19. The method according to claim 14 wherein the medium is air.

20. The method according to claim 14 further comprising a wicking material layer adjacent the interior wall.

21. The method according to claim 14 further comprising a reinforcing material layer adjacent the exterior wall.

22. The method according to claim 14 wherein the support section and pressure adjustment section comprise a single chamber.

23. The method according to claim 14 wherein the pressure adjustment section is interconnected with the support section through at least one medium transfer channel.

24. The method according to claim 14 further comprising a plurality of interspaced non-support regions in the support section.

25. The method according to claim 14 wherein the support section comprises:
a lower portion, wherein at least a portion of the interior wall of the lower portion contacts at least a portion of a lower region of a body part;
an intermediate portion, wherein at least a portion of the interior wall of the intermediate portion contacts at least a portion of an intermediate region of the body part; and
an upper portion, wherein at least a portion of the interior wall of the upper portion contacts at least a portion of an upper region of the body part.

26. The method of claim 14 further comprising attaching at least a portion of a first edge of the support section to at least a portion of a second edge of the support section with one or more securing devices.

27. A protective and pressure normalizing device comprising
a support member having a support section and a pressure adjustment section, the support section and the pressure adjustment section have an exterior wall and an interior wall;
the support section has at least at least two end apertures, and a gap aperture that extends between the two end apertures;

the gap aperture and the end apertures are capable of receiving at least a portion of an object;
a first chamber is defined by the exterior wall and the interior wall, and is capable of receiving a medium;
the pressure adjustment section extends away from and above at least one end aperture and support section and in a first position of the protective and pressure normalizing device (a) the entire interior wall of the pressure adjustment section is unfolded and (b) the medium is contained within the first chamber, and the medium within the support section applies a first pressure to the exterior and interior walls;
the first pressure can be adjusted by folding and attaching at least a portion of the exterior wall of the pressure adjustment section to the exterior wall of the pressure adjustment section or the exterior wall of the support section.

28. The device according to claim 27 wherein the pressure adjustment section extends from a distal aperture or a proximal aperture of the support section and is movable toward a joint aperture of the support section.

29. The device according to claim 28 wherein the pressure adjustment section is movable to extend adjacent the joint aperture of the support section.

30. The device according to claim 27 wherein the pressure adjustment section further comprises an attachment device for attaching at least a first portion of the pressure adjustment section to at least a portion of the support section or at least a second portion of the pressure adjustment section.

31. The device according to claim 27 further comprising a wicking material layer adjacent the interior wall.

32. The device according to claim 27 further comprising a reinforcing material layer adjacent the exterior wall.

33. The device according to claim 27 wherein the chamber is filled with the medium to a predetermined internal pressure.

34. The device according to claim 27 wherein the medium is air.

35. The device according to claim 27 wherein the support section and pressure adjustment section comprise a single chamber.

36. The device according to claim 27 wherein the pressure adjustment section is interconnected with the support section through at least one medium transfer channel.

37. The device according to claim 27 further comprising a plurality of interspaced non-support regions in the support section.

38. The device according to claim 27 wherein the support section comprises:
a lower portion, wherein at least a portion of the interior wall of the lower portion contacts at least a portion of a lower region of a body part;
an intermediate portion, wherein at least a portion of the interior wall of the intermediate portion contacts at least a portion of an intermediate region of the body part; and
an upper portion, wherein at least a portion of the interior wall of the upper portion contacts at least a portion of an upper region of the body part.

39. The device of claim 27 further comprising one or more securing devices, wherein the one or more securing devices attach at least a portion of a first edge of the support section to at least a portion of a second edge of the support section.

* * * * *